United States Patent
Mr et al.

(10) Patent No.: US 11,801,487 B2
(45) Date of Patent: Oct. 31, 2023

(54) AUTOMATIC RECHARGER BRINE PREPARATION FROM A SALT BAG

(71) Applicant: Medtronic, Inc., Minneapolis, MN (US)

(72) Inventors: Kirankumar Mr, Bangalore (IN); Muhammed Mashal P K, Bangalore (IN)

(73) Assignee: Mozarc Medical US LLC, Minneapolis, MN (US)

( * ) Notice: Subject to any disclaimer, the term of this patent is extended or adjusted under 35 U.S.C. 154(b) by 73 days.

(21) Appl. No.: 17/152,404

(22) Filed: Jan. 19, 2021

(65) Prior Publication Data
US 2022/0226798 A1    Jul. 21, 2022

(51) Int. Cl.
| | | |
|---|---|---|
| *B01J 20/02* | (2006.01) | |
| *B01J 20/06* | (2006.01) | |
| *B01J 20/28* | (2006.01) | |
| *B01J 41/02* | (2006.01) | |
| *B01J 20/34* | (2006.01) | |
| *B01J 39/09* | (2017.01) | |
| *B01J 39/12* | (2006.01) | |

(52) U.S. Cl.
CPC ....... *B01J 20/0211* (2013.01); *B01J 20/0292* (2013.01); *B01J 20/06* (2013.01); *B01J 20/28052* (2013.01); *B01J 20/3433* (2013.01); *B01J 20/3475* (2013.01); *B01J 20/3483* (2013.01); *B01J 39/09* (2017.01); *B01J 39/12* (2013.01); *B01J 41/02* (2013.01)

(58) Field of Classification Search
CPC ........ B01J 20/02; B01J 20/0211; B01J 39/09; B01J 20/0292; B01J 20/06; B01J 20/28052; B01J 20/3433; B01J 20/3475; B01J 20/3483; B01J 39/12; B01J 41/02
USPC ........................................................ 502/400
See application file for complete search history.

(56) References Cited

U.S. PATENT DOCUMENTS

| | | | |
|---|---|---|---|
| 2020/0061269 A1* | 2/2020 | Dutta | .............. B01J 20/3475 |
| 2022/0226552 A1* | 7/2022 | Mr | ................... A61M 1/1696 |
| 2022/0226801 A1* | 7/2022 | Mr | ................... B01J 20/3475 |

* cited by examiner

*Primary Examiner* — Edward M Johnson
(74) *Attorney, Agent, or Firm* — Hahn & Associates (57) ABSTRACT

Systems and methods for generating a brine solution using a salt bag for recharging zirconium phosphate in a reusable sorbent module are provided. The salt bag can be a double layer bag. An inner water permeable bag can contain solid salts and can be surrounded by an outer water impermeable bag. Water can be added to dissolve the salts in the inner bag and the resulting solution can be collected as a brine solution for use in recharging the zirconium phosphate.

20 Claims, 7 Drawing Sheets

AUTOMATIC RECHARGER BRINE PREPARATION FROM A SALT BAG

FIELD

The disclosure relates to systems and methods for generating a brine solution using a salt bag for recharging zirconium phosphate in a reusable sorbent module. The salt bag can be a double layer bag. An inner water permeable bag can contain solid salts and can be surrounded by an outer water impermeable bag. Water can be added to dissolve the salts in the inner bag and the resulting solution can be collected as a brine solution for use in recharging the zirconium phosphate.

BACKGROUND

Sorbent based dialysis systems can use zirconium phosphate as a sorbent material to remove potassium, calcium, and magnesium ions from spent dialysate. The zirconium phosphate is generally provided in a sorbent cartridge with other sorbent materials. After use, the spent zirconium phosphate is disposed or removed from the sorbent cartridge for further processing. However, removing spent zirconium phosphate from a sorbent cartridge, separating the zirconium phosphate from other sorbent materials, and processing the spent zirconium phosphate can require significant time and expense. Further, large quantities of solutions for processing the spent zirconium phosphate can be required along with any necessary infrastructure, storage, and transportation. Expensive manufacturing lines and plants may also be required to generate premade solutions for use in processing the zirconium phosphate.

Hence, there is a need for systems and methods that can recharge zirconium phosphate within a reusable sorbent module. There is further a need for systems and methods for generating a recharge solution necessary for recharging the zirconium phosphate, and in particular, brine solutions. There is a need for systems and methods that can generate the brine solution on-line and quickly, reducing the storage needs and time required for preparation.

SUMMARY OF THE INVENTION

The problem to be solved by the present invention is online preparation of a brine solution for use in recharging sorbent materials. The solution is to include sodium chloride and sodium acetate in a salt canister. The sodium chloride and sodium acetate can be dissolved when needed to generate the brine solution.

The first aspect of the invention relates to a system. In any embodiment, the system can include a sorbent recharger; the sorbent recharger having: i) a receiving compartment for a zirconium phosphate sorbent module; ii) at least a first fluid line fluidly connectable to an inlet of the zirconium phosphate sorbent module in the receiving compartment; iii) at least a second fluid line fluidly connectable to an outlet of the zirconium phosphate sorbent module; and iv) at least one pump. The system can also include a brine container fluidly connectable to the first fluid line; a salt bag; the salt bag having an inlet fluidly connectable to a water source and an acetic acid source; and an outlet fluidly connectable to the brine container; the salt bag containing sodium chloride and sodium acetate; and a control system; the control system programmed to: i) pump a preset volume of fluid from the water source through the salt bag; ii) recirculate fluid in a first flow path from the outlet of the salt bag to the brine container and then to the inlet of the salt bag; and to iii) pump a preset volume of acetic acid into the first flow path.

In any embodiment, the salt bag can be a double layer bag comprising an outer bag that is water impermeable and an inner bag that is at least partly water permeable.

In any embodiment, the sodium chloride and sodium acetate can be initially in the inner bag of the salt bag.

In any embodiment, the inner bag can have a water impermeable portion at a top of the inner bag.

In any embodiment, the inlet of the salt bag can be positioned on a top of the salt bag, and the outlet of the salt bag can be positioned on a bottom of the salt bag.

In any embodiment, the inlet of the salt bag can be connected to an interior of the inner bag; and the outlet of the salt bag can be connected to an exterior of the inner bag.

In any embodiment, the control system can be further programmed to pump fluid from the brine container through the zirconium phosphate sorbent module.

In any embodiment, the control system can be programmed to recirculate fluid in the first flow path until a homogeneous solution is formed in the first flow path.

In any embodiment, the control system can be programmed to recirculate fluid in the first flow path for a preset period of time.

In any embodiment, the sodium chloride and sodium acetate can initially be solid.

In any embodiment, the salt bag further can include a spring-loaded valve at the inlet.

In any embodiment, the salt bag further can include a spring-loaded valve at the outlet.

The features disclosed as being part of the first aspect of the invention can be in the first aspect of the invention, either alone or in combination, or follow any arrangement or permutation of any one or more of the described elements. Similarly, any features disclosed as being part of the first aspect of the invention can be in a second, third, fourth, or fifth aspect of the invention described below, either alone or in combination, or follow any arrangement or permutation of any one or more of the described elements.

The second aspect of the invention relates to a method for generating a brine solution for recharging zirconium phosphate. In any embodiment, the method can include the steps of: pumping water from a water source to a salt bag through an inlet of a salt bag; the salt bag containing sodium chloride and sodium acetate; recirculating fluid from an outlet of the salt bag, to a brine container, and back to the inlet of the salt bag in a first flow path; pumping acetic acid into the first flow path; and collecting fluid from the first flow path into the brine container to generate the brine solution.

In any embodiment, the salt bag can be a double layer bag comprising an outer bag that is water impermeable and an inner bag that is at least partly water permeable.

In any embodiment, the sodium chloride and sodium acetate can be initially in the inner bag of the salt bag.

In any embodiment, the inner bag can have a water impermeable portion at a top of the inner layer.

In any embodiment, the inlet of the salt bag can be positioned on a top of the salt bag, and the outlet of the salt bag can be positioned on a bottom of the salt bag.

In any embodiment, the inlet of the salt bag can be fluidly connected to an interior of the inner bag; and the outlet of the salt bag can be connected to an exterior of the inner bag.

In any embodiment, the brine container can be fluidly connected to a sorbent recharger; and the method can include the step of pumping the brine solution through a zirconium phosphate sorbent module in the sorbent recharger.

In any embodiment, the fluid can be recirculated in the first flow path until a homogenous solution is generated.

In any embodiment, the fluid can be recirculated in the first flow path for a preset period of time.

In any embodiment, the sodium chloride and sodium acetate can be initially solid.

The features disclosed as being part of the second aspect of the invention can be in the second aspect of the invention, either alone or in combination, or follow any arrangement or permutation of any one or more of the described elements. Similarly, any features disclosed as being part of the second aspect of the invention can be in the first, third, fourth, or fifth aspect of the invention described below, either alone or in combination, or follow any arrangement or permutation of any one or more of the described elements.

The third aspect of the invention is drawn to a salt bag. In any embodiment, the salt bag can include a water impermeable outer bag; a water permeable inner bag; an inlet fluidly connectable to a water source; and an outlet fluidly connectable to a brine container; the salt bag containing sodium chloride and sodium acetate.

In any embodiment, the salt bag can include a spring-loaded valve at the inlet.

In any embodiment, the salt bag can include a spring-loaded valve at the outlet.

In any embodiment, the inner bag can have a water impermeable portion at a top of the inner bag.

In any embodiment, the inlet can be connected to an interior of the inner bag; and the outlet can be connected to an exterior of the inner bag.

The features disclosed as being part of the third aspect of the invention can be in the third aspect of the invention, either alone or in combination, or follow any arrangement or permutation of any one or more of the described elements. Similarly, any features disclosed as being part of the third aspect of the invention can be in the first, second, fourth, or fifth aspect of the invention described below, either alone or in combination, or follow any arrangement or permutation of any one or more of the described elements.

The fourth aspect of the invention is drawn to a sorbent recharger. In any embodiment, the sorbent recharger can include at least one inlet fluidly connectable to a water source; at least one inlet fluidly connectable to a brine container; and at least one outlet fluidly connectable to the salt bag of the third aspect of the invention.

In any embodiment, the sorbent recharger can include a control system programmed to: i) pump a preset volume of fluid from the water source into the salt bag; ii) recirculate fluid in a first flow path from the outlet of the salt bag to the brine container and then to the inlet of the salt bag; and to iii) pump a preset volume of acetic acid into the first flow path.

In any embodiment, the control system can be programmed to recirculate fluid in the first flow path until a homogeneous solution is generated in the first flow path.

In any embodiment, the control system can be programmed to recirculate fluid in a first flow path for a preset period of time.

The features disclosed as being part of the fourth aspect of the invention can be in the fourth aspect of the invention, either alone or in combination, or follow any arrangement or permutation of any one or more of the described elements. Similarly, any features disclosed as being part of the fourth aspect of the invention can be in the first, second, third, or fifth aspect of the invention described below, either alone or in combination, or follow any arrangement or permutation of any one or more of the described elements.

The fifth aspect of the invention is drawn to a brine container. In any embodiment, the brine container can include an inlet fluidly connectable to the salt bag of the third aspect of the invention and an outlet fluidly connectable to a sorbent recharger.

The features disclosed as being part of the fifth aspect of the invention can be in the fifth aspect of the invention, either alone or in combination, or follow any arrangement or permutation of any one or more of the described elements. Similarly, any features disclosed as being part of the fifth aspect of the invention can be in the first, second, third, or fourth aspect of the invention described below, either alone or in combination, or follow any arrangement or permutation of any one or more of the described elements.

DETAILED DESCRIPTION

Unless defined otherwise, all technical and scientific terms used have the same meaning as commonly understood by one of ordinary skill in the art.

The articles "a" and "an" are used to refer to one to over one (i.e., to at least one) of the grammatical object of the article. For example, "an element" means one element or over one element.

The term "acetic acid" refers to $CH_3CO_2H$ in an aqueous solution.

An "acetic acid source" is a solid, fluid, or concentrate source from which acetic acid or an acetic acid solution can be obtained.

The term "bottom" refers to a portion of a component intended to be at a lower elevation than a "top" during normal use of the component.

A "brine container" is a container for containing a brine solution.

A "brine solution" is a solution containing sodium chloride, an acid, and the sodium salt of the acid.

To "collect" a fluid refers to flowing a volume of the fluid into a container.

The term "comprising" includes, but is not limited to, whatever follows the word "comprising." Use of the term indicates the listed elements are required or mandatory but that other elements are optional and may be present.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "containing" refers to a substance that is within a component or container.

A "control system" can be a combination of components that act together to maintain a system to a desired set of performance specifications. The control system can use processors, memory and computer components configured to interoperate to maintain the desired performance specifications. The control system can also include fluid or gas control components, and solute control components as known within the art to maintain performance specifications.

The term "double layer" refers to a component having both an outer layer in contact with the environment outside of the component and an inner layer that is within the outer layer.

The term "exterior" refers to an area outside of a given component or system.

A "flow path" is a pathway through which a fluid, gas, or combinations thereof travel.

A "fluid" is a liquid substance optionally having a combination of gas and liquid phases in the fluid. Notably, a liquid, as used herein, can therefore also have a mixture of gas and liquid phases of matter.

A "fluid line" can refer to a tubing or conduit through which a fluid or fluid containing gas can pass. The fluid line can also contain air during different modes of operation such as cleaning or purging of a line.

The term "fluidly connectable" refers to the ability of providing for the passage of fluid, gas, or combination thereof, from one point to another point. The ability of providing such passage can be any connection, fastening, or forming between two points to permit the flow of fluid, gas, or combinations thereof. The two points can be within or between any one or more of compartments of any type, modules, systems, components, and rechargers.

The term "fluidly connected" refers to a particular state such that the passage of fluid, gas, or combination thereof, is provided from one point to another point. The connection state can also include an unconnected state, such that the two points are disconnected from each other to discontinue flow. It will be further understood that the two "fluidly connectable" points, as defined above, can form a "fluidly connected" state. The two points can be within or between any one or more of compartments, modules, systems, components, and rechargers, all of any type.

The terms "generate," "generating," "is generated," and the like refer to forming a solution or substance from constituent parts.

The term "homogeneous solution" refers to an aqueous solution wherein the concentration of solutes is substantially identical at all parts of the solution.

The term "initially" refers to a state of a component or system prior to a process.

The term "inlet" can refer to a portion of container, flow path, or component through which fluid, gas, or a combination thereof can be drawn into the container, flow path, or component.

The term "inner bag" refers to a bag that is entirely within an outer layer of a double layer component.

The term "interior" refers to an area inside of a given component or system.

The term "outer bag" refers to a bag that surrounds an inner layer of a double layer component.

The term "outlet" can refer to a portion of container, flow path, or component through which fluid, gas, or a combination thereof can be drawn out of the container, flow path, or component.

A "preset period of time" is a length of time that is set prior to a process or step.

The term "preset volume" refers to an amount of fluid determined prior to a process.

The term "processor" or "microprocessor" as used is a broad term and is to be given an ordinary and customary meaning to a person of ordinary skill in the art. The term refers without limitation to a computer system, state machine, processor, or the like designed to perform arithmetic or logic operations using logic circuitry that responds to and processes the basic instructions that drive a computer. In any embodiment of the first, second, third, and fourth invention, the terms can include ROM ("read-only memory") and/or RAM ("random-access memory") associated therewith.

The term "programmed," when referring to a processor, can mean a series of instructions that cause a processor to perform certain steps.

The term "pump" refers to any device that causes the movement of fluids or gases by applying suction or pressure.

A "receiving compartment" can be a compartment, section, or chamber of any device or components. In one non-limiting example, the receiving compartment can be within a sorbent recharger into which a sorbent module can be positioned to be recharged.

"Recharging" refers to treating a sorbent material to restore the functional capacity of the sorbent material to put the sorbent material back into a condition for reuse or use in a new dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged."

To "recirculate" refers to moving fluid in a flow loop from a first point through the flow loop and back to the first point.

A "salt bag" is a bag designed to hold solid salts for generation of a brine solution. The salt bag can include an inner porous bag in which the solid salts are placed, and an outer non-porous bag into which a solution can flow from the inner bag.

The term "sodium acetate" refers to $CH_3CO_2Na$ either solid or in an aqueous solution.

The term "sodium chloride" refers to NaCl either solid or in an aqueous solution.

The term "solid" refers to a material in the solid phase of matter, and can include crystalline, powdered, or any other form of solid material.

A "sorbent module" means a discreet component of a sorbent cartridge. Multiple sorbent cartridge modules can be fitted together to form a sorbent cartridge of two, three, or more sorbent cartridge modules. The "sorbent cartridge module" or "sorbent module" can contain any selected materials for use in sorbent dialysis and may or may not contain a "sorbent material" or adsorbent, but less than the full complement of sorbent materials needed. In other words, the "sorbent cartridge module" or "sorbent module" generally refers to the use of the "sorbent cartridge module" or "sorbent module" in sorbent-based dialysis, e.g., REDY (REcirculating DYalysis), and not that a "sorbent material" that is necessarily contained in the "sorbent cartridge module" or "sorbent module."

A "sorbent recharger" or "recharger" is an apparatus designed to recharge at least one sorbent material.

A "spring-loaded valve" is a valve controlled by a spring, the valve opens or closes when pressure is placed on the spring.

The term "top" refers to a portion of a component intended to be at a higher elevation than a "bottom" during normal use of the component.

The term "water impermeable" refers to a material that substantially prevents water or aqueous solutions from passing through the component.

The term "water permeable" refers to the ability of water and aqueous solutions to pass through a material.

The term "water source" refers to any source from which potable or non-potable water can be obtained.

"Zirconium phosphate" is a sorbent material that removes cations from a fluid, exchanging the removed cations for different cations.

A "zirconium phosphate sorbent module" is a sorbent module that contains zirconium phosphate.

Brine Preparation from a Salt Bag

Figure 1A:
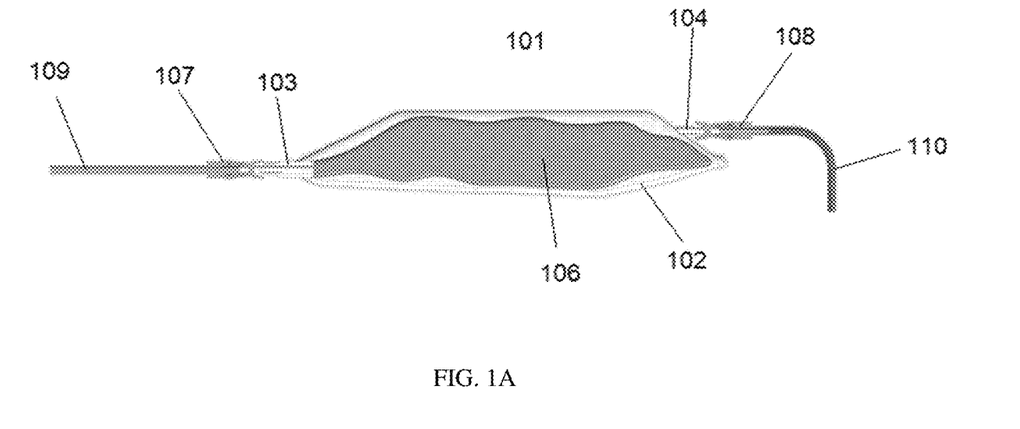
FIGS. 1A-D illustrate a salt bag for preparation of a brine solution.
Figure 1B:
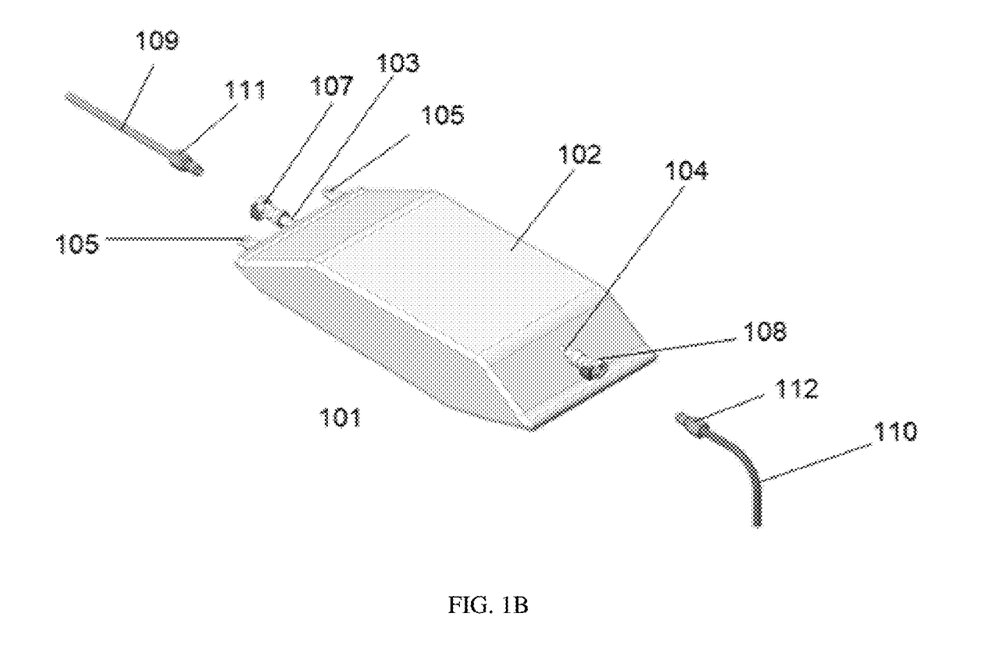
Figure 1C:
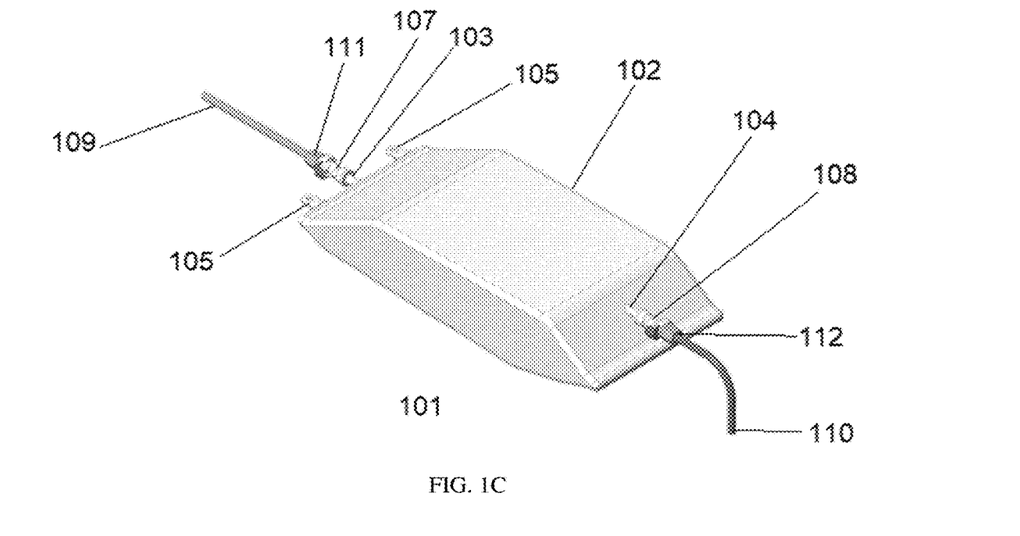
Figure 1D:
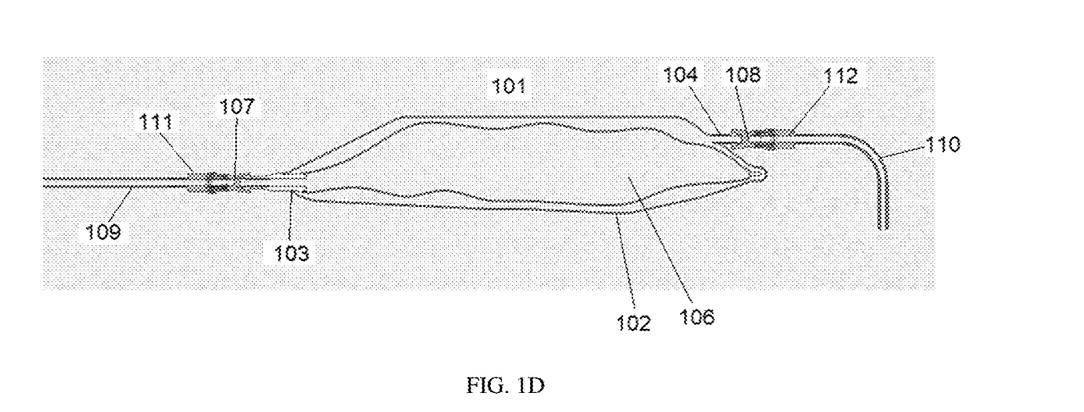

FIGS. 1A-D illustrate a salt bag that can be used to generate brine for recharging zirconium phosphate in a reusable zirconium phosphate sorbent module. FIG. 1A is a transparent view of a salt bag 101, FIG. 1B is a perspective view of the salt bag 101 disconnected from fluid lines, FIG. 1C is a perspective view of the salt bag 101 connected to fluid lines, and FIG. 1D is a transparent view of the salt bag 101 showing details of the connections.

As illustrated in FIG. 1A, the salt bag 101 can include an outer bag 102 and an inner bag 106. Initially, sodium chloride and sodium acetate can be placed in inner bag 106. In certain embodiments, the sodium chloride and sodium acetate can be solid sodium chloride and solid sodium acetate. To generate a brine solution, a preset volume of water can be added from a water source through fluid line 109, spring-loaded valve 107, through inlet 103 of the salt bag 101 and into an interior of the inner bag 106. The water can dissolve the sodium acetate and sodium chloride in inner bag 106 to generate a brine solution. The inner bag 106 can be a porous, water permeable bag, while outer bag 102 is water impermeable. The pore size of inner bag 106 can be small enough to prevent solid sodium chloride and sodium acetate from entering outer bag 102, but can allow water and brine solution into outer bag 102. A person of ordinary skill in the art will be able to determine a pore size to prevent solid material from exiting inner bag 106 but allowing the brine solution through. The generated brine solution can exit inner bag 106, enter outer bag 102 and leave the salt bag 101 through outlet 104. The outlet 104 of the salt bag 101 is positioned exterior to inner bag 106 and can be fluidly connectable to a brine container (not shown) through spring-loaded valve 108 and fluid line 110. The generated brine solution can be collected in the brine container. The brine solution can be recirculated back to inlet 103 of the salt bag 101, through the outlet 104, and back through the brine container. The brine solution can be recirculated for a preset period of time, or until a homogeneous mixture is formed in the recirculation flow path.

FIG. 1B shows the salt bag 101 disconnected from fluid lines 109 and 110. Fluid line 109 can connect to the inlet 103 of salt bag 101 at spring-loaded valve 107. Similarly, fluid line 110 can connect to the outlet 104 of salt bag 101 at spring-loaded valve 108. When the inlet 103 is connected to fluid line 109, connector 111 applies pressure to spring loaded valve 107, opening the valve and allowing fluid to flow in or out of salt bag 101. When the outlet 104 is connected to fluid line 110, connector 112 applies pressure to spring loaded valve 108, opening the valve and allowing fluid to flow in or out of salt bag 101. Spring loaded valve 107 and spring-loaded valve 108 also operate as non-return valves during salt preparation, avoiding backflow of salt and fluid until the salt bag 101 is connected to the system. Fluid flow in an out of the salt bag 101 can be arrested due to spring loaded valve 107 and spring-loaded valve 108. Spring-loaded valve 107 and spring-loaded valve 108 prevent the salt or fluids inside the salt bag 101 from spilling out. When the salt bag 101 is not connected to the system, spring loaded valve 107 and spring-loaded valve 108 are closed, preventing any fluid movement into or out of salt bag 101.

FIG. 1C shows the salt bag 101 after connection to fluid lines 109 and 110. Connector 111 has been inserted into spring loaded valve 107, allowing fluid to enter the salt bag 101 through inlet 103. Connector 112 has been inserted into spring loaded valve 108, allowing fluid to exit salt bag 101 through outlet 104. In certain embodiment, flaps 105 can be included for aid in mounting the salt bag 101. Hooks can be included on or near a sorbent recharger and inserted through flaps 105 for mounting the salt bag 101. However, the salt bag 101 can be mounted using any other system known to those in the art.

As illustrated in FIG. 1D, the inlet 103 of salt bag 101 can connect to an interior of inner bag 106. Fluid entering salt bag 101 from fluid line 109 flows directly into the inner bag 106 rather than outer bag 102. include an outer bag 102 and an inner bag 106. The outlet 104 of the salt bag 101 is only fluidly connected to the outer bag 102. Fluid exiting the salt bag 101 first passes through the walls of inner bag 102 and then enters fluid line 110 through outlet 104.

Figure 2:
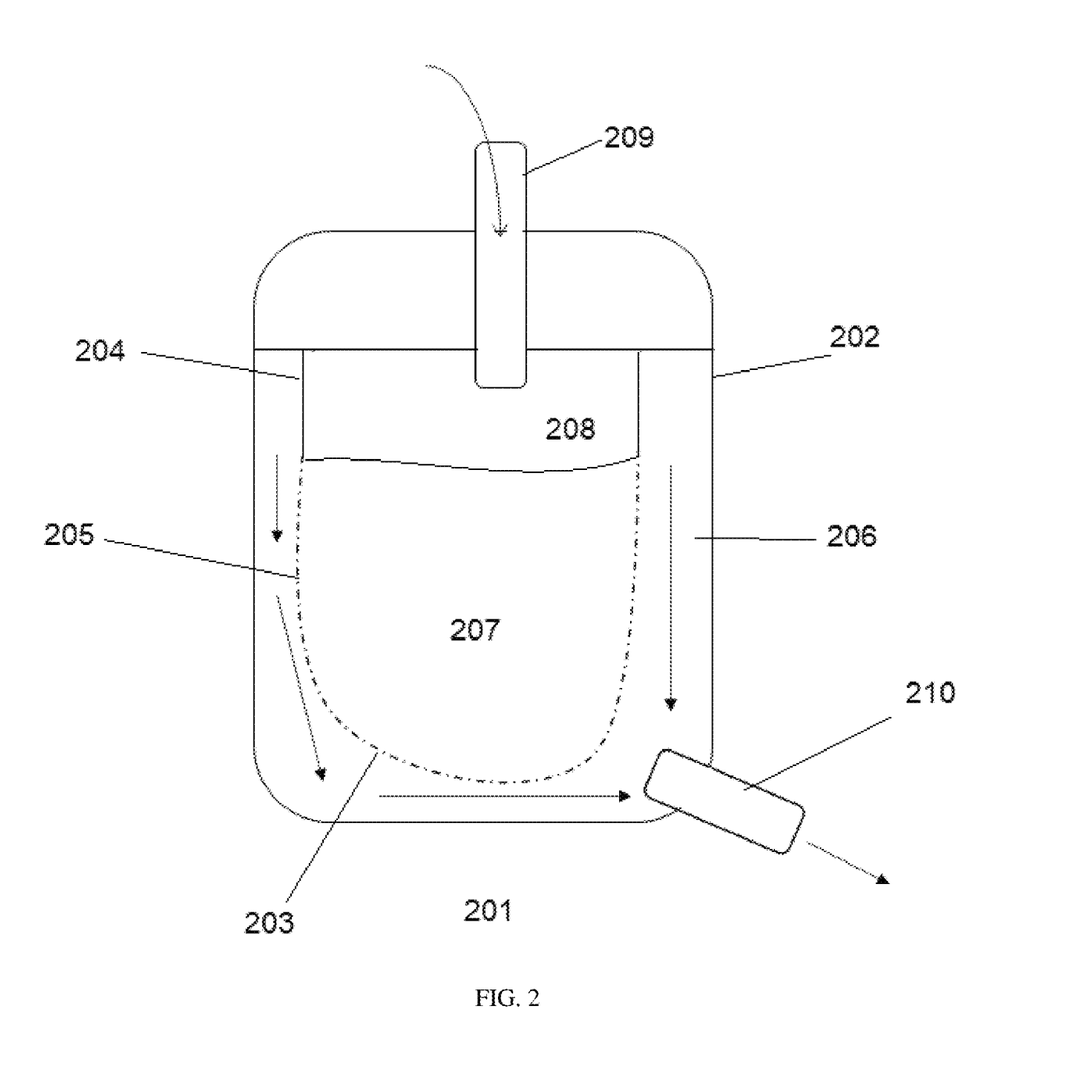
FIG. 2 illustrates a transparent view of a salt bag for preparation of a brine solution.

FIG. 2 is a different transparent view of a salt bag 201. The salt bag 201 can include an inner bag 203 having a porous, water permeable wall 205. In certain embodiments, the inner bag 203 can include a top portion 208 having a water impermeable wall 204. The sodium acetate and sodium chloride can be placed in the bottom portion 207 of the inner bag 203, while a preset volume of water from a water source is added through inlet 209 into the top portion 208 of the inner bag 203. The water impermeable wall 205 at the top portion 208 of the inner bag 203 prevents water from escaping the inner bag 203 prior to contacting the sodium acetate and sodium chloride in the bottom portion 207 of the inner bag 203. In certain embodiments, the non-porous top portion 208 of the inner bag 203 can cover about 30% of the inner bag 203, while the porous bottom portion 207 can cover the other 70% of the inner bag 203.

The inner bag 203 is surrounded by a water impermeable outer bag 202. Water can exit the inner bag 203 through porous walls 205 and enter a space 206 between the inner bag 203 and outer bag 202. The water in the space 206 between the inner bag 203 and outer bag 202 exits the salt bag 201 through outlet 210 to be recirculated in a flow path back to inlet 209 and eventually collected in a brine container.

In certain embodiments, the inner bag 203 can be constructed from a porous polymer. For example, polypropylene, polyethylene, or high-density polyethylene can be used. The non-porous outer bag 202 can be constructed from polypropylene or high-density polyethylene. However, other materials or polymers can be used for either bag. The porous inner bag 203 should have a pore size small enough to retain solid sodium chloride and sodium acetate in the inner bag 203, while allowing dissolved water and sodium chloride and sodium acetate to pass through the walls of the inner bag 203.

The required size of the salt bag 201 depends on the amount of brine solution desired and can be determined by a person of ordinary skill in the art. As a non-limiting example, the inner bag 203 of salt bag 201 can be sized to hold between 1.5-2.0 kg of sodium acetate and sodium chloride with 200-300 mL left of water filling capacity. The space 206 between the inner bag 203 and outer bag 202 can have a volume of about 200-300 mL. As additional water is added to the salt bag 201, the solution in space 206 is forced out to the brine container (not shown). The volume of water added can be varied to generate a brine solution having a desired sodium concentration. In certain embodiments, about 5 L of water can be used to generate the brine solution. However, the amount of water used can be varied depending on the desired brine solution concentration and the amount of salt used.

Figure 3:
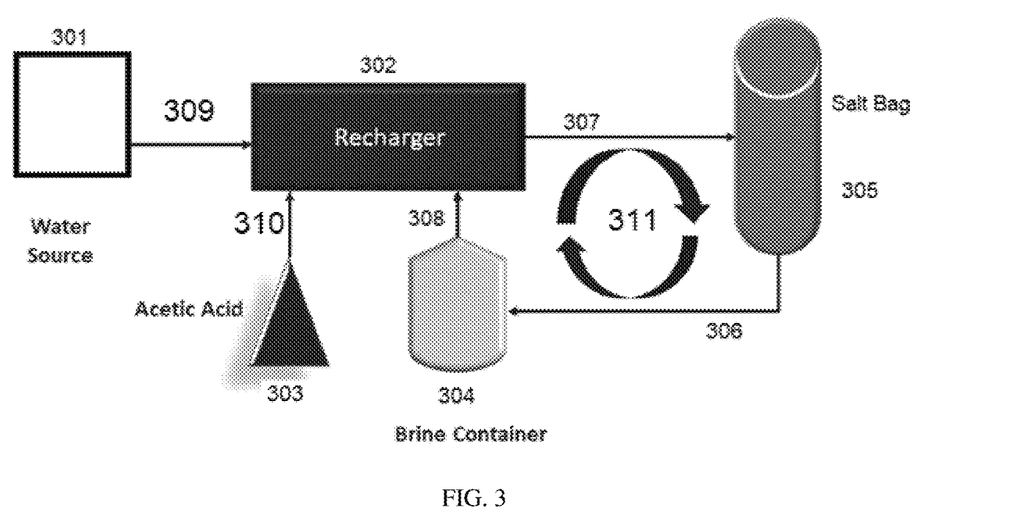
FIG. 3 illustrates a sorbent recharger system using a salt bag.

FIG. 3 is a generalized diagram of a sorbent recharger system using the described salt bag 305. As described, the salt bag 305 can include sodium acetate and sodium chloride in any amounts within a porous, water permeable inner bag (not shown). Water from water source 301 can be pumped into an inlet of the salt bag 305, which is fluidly connected to the inner bag. In certain embodiments, the water source can be fluidly connected to a sorbent recharger 302. The water can be pumped from water source 301, through line 309 into the sorbent recharger 302 and then into the salt bag 305 through fluid line 307. Alternatively, a separate fluid line (not shown) can connect the water source 301 to the inlet of salt bag 305.

The water pumped into salt bag 305 can dissolve the sodium acetate and sodium chloride and enter a space between the porous inner bag and the non-porous outer bag of salt bag 305. The resulting solution can be pumped through an outlet of the salt bag 305 into brine container 304. To ensure complete dissolution of the sodium acetate and sodium chloride and a homogeneous brine solution, the solution can be recirculated through a flow path as shown by arrows 311. The brine solution can be pumped from the outlet of the salt bag 305 into brine container 304 through fluid line 306, back into recharger 302 through fluid line 308, and then back to the inlet of the salt bag 305 through fluid line 307. The salt bag 305, fluid line 306, brine container 304, fluid line 308, recharger 302, and fluid line 307 define a recirculation flow path. The solution can be pumped through the recirculation flow path until a homogeneous solution is formed, or for some preset period of time that is long enough to ensure formation of a homogenous solution. The preset period of time can be any time long enough to ensure complete dissolution and homogeneity. In certain embodiments, the preset period of time can be between 20 and 45 minutes. Additionally, or alternatively, one or more sensors, such as conductivity sensors, can be included to ensure that the generated brine solution has the proper concentrations of sodium chloride and sodium acetate.

The brine solution, once formed, can be used to recharge zirconium phosphate in a zirconium phosphate sorbent module. The brine solution can replace cations that were bound to the zirconium phosphate during dialysis treatment with sodium and hydrogen ions. The final ratio of sodium to hydrogen ions on the recharged zirconium phosphate is a function of the pH and sodium concentration of the brine solution. As such, the sodium/hydrogen ratio of the recharged zirconium phosphate can be controlled by controlling the pH of the brine solution used in recharging. Acetic acid from acetic acid source 303 can be added to the recirculation flow path while the brine is being recirculated to adjust the pH of the brine solution. Acetic acid can be pumped from acetic acid source 303 through fluid line 310 into the sorbent recharger 302 for addition to the recirculating flow path. A control system (not shown) can control one or more pumps and one or more valves within the sorbent recharger 302 to generate a brine solution having a specified pH by adding a volume of acetic acid from the acetic acid source 303. Using a known amount of sodium chloride and sodium acetate in salt bag 305 and adding a set amount of water from water source 301 can provide a known sodium concentration in the resulting brine solution. The amount of acetic acid added from acetic acid source 303 can be controlled by the control system to generate a brine solution having a desired pH.

To recharge the zirconium phosphate in a zirconium phosphate sorbent module, the control system can control one or more pumps (not shown) and/or valves (not shown) to pump the generated brine solution from brine source 304, through fluid line 308, into sorbent recharger 302 where the brine solution is passed through the zirconium phosphate sorbent module.

Table 1 shows a non-limiting example of a brine solution for recharging zirconium phosphate that can be made using the described salt bag system.

TABLE 1

ZP Recharge—Brine Solution Preparation

| Description | Sodium chloride | Sodium Acetate, trihydrate | Acetic Acid | Water |
|---|---|---|---|---|
| Conc M | 4.70 | 0.40 | 0.40 | N/A |
| Mol wt | 58.50 | 136.00 | 60.05 | N/A |
| Mix density (kg/l) @25° C. | | 1.19 | | |
| Individual density (kg/l) @25° C. | 2.16 | 1.45 | 1.05 | 1.00 |
| Total Volume (L) | | 6.20 | | |
| Total weight (kg) | | 7.38 | | |
| Individual weight (kg) | 1.70 | 0.34 | 0.15 | 5.19 |
| Individual volume (L) | N/A | N/A | 0.14 | 5.20 |

The brine solution described in Table 1 uses 5.20 L of water, which is added to a salt bag containing 1.70 kg of sodium chloride and 0.34 kg of sodium acetate trihydrate. 0.14 L of acetic acid can be added during generation of the brine solution, as described. The resulting brine solution has a sodium chloride concentration of 4.70 M, a sodium acetate concentration of 0.40 M, and an acetic acid concentration of 0.40 M. However, as described, brine solutions having a higher or lower pH can be generated by adding more or less acetic acid or sodium acetate. A person of ordinary skill in the art will understand that the ratio of sodium chloride to sodium acetate used can vary depending on the needs of the user. The sodium concentration of the brine solution can be controlled by using more or less sodium chloride and sodium acetate or by varying the volume of water added to the salt canister in forming the brine solution as would be understood by one of ordinary skill in the art. One or more conductivity sensors can be used to ensure complete dissolution and homogeneity. The conductivity of the generated brine solution will vary based on the concentrations of each solute. However, the conductivity of the solution shown in Table 1 should be within 180-240 mS/cm at 25° C.

Figure 4A:
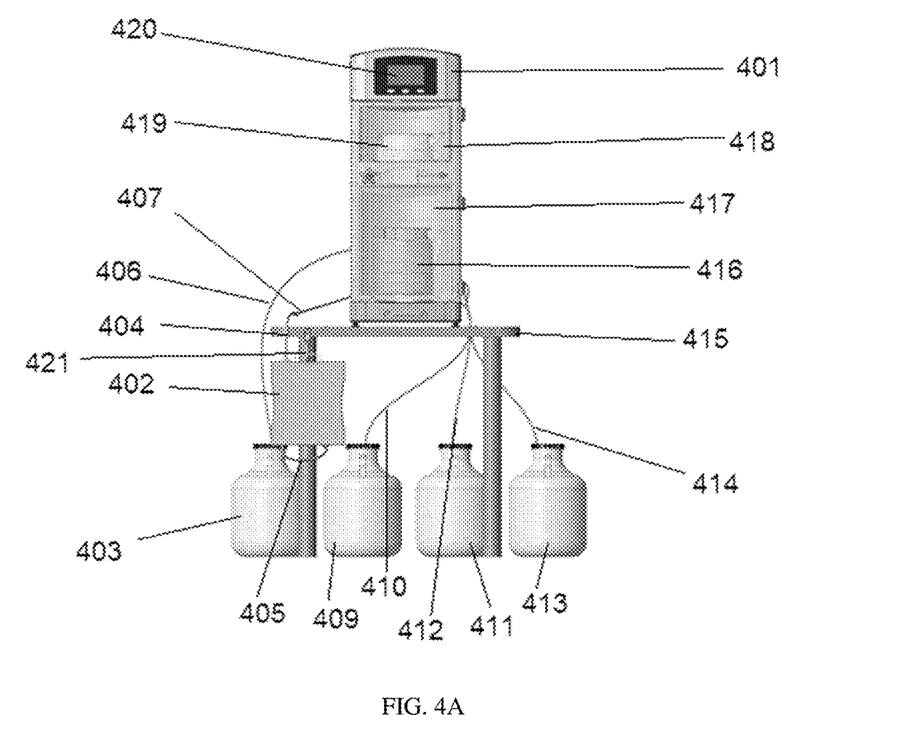
FIGS. 4A-B illustrate a sorbent recharger for recharging sorbent materials in reusable sorbent modules.
Figure 4B:
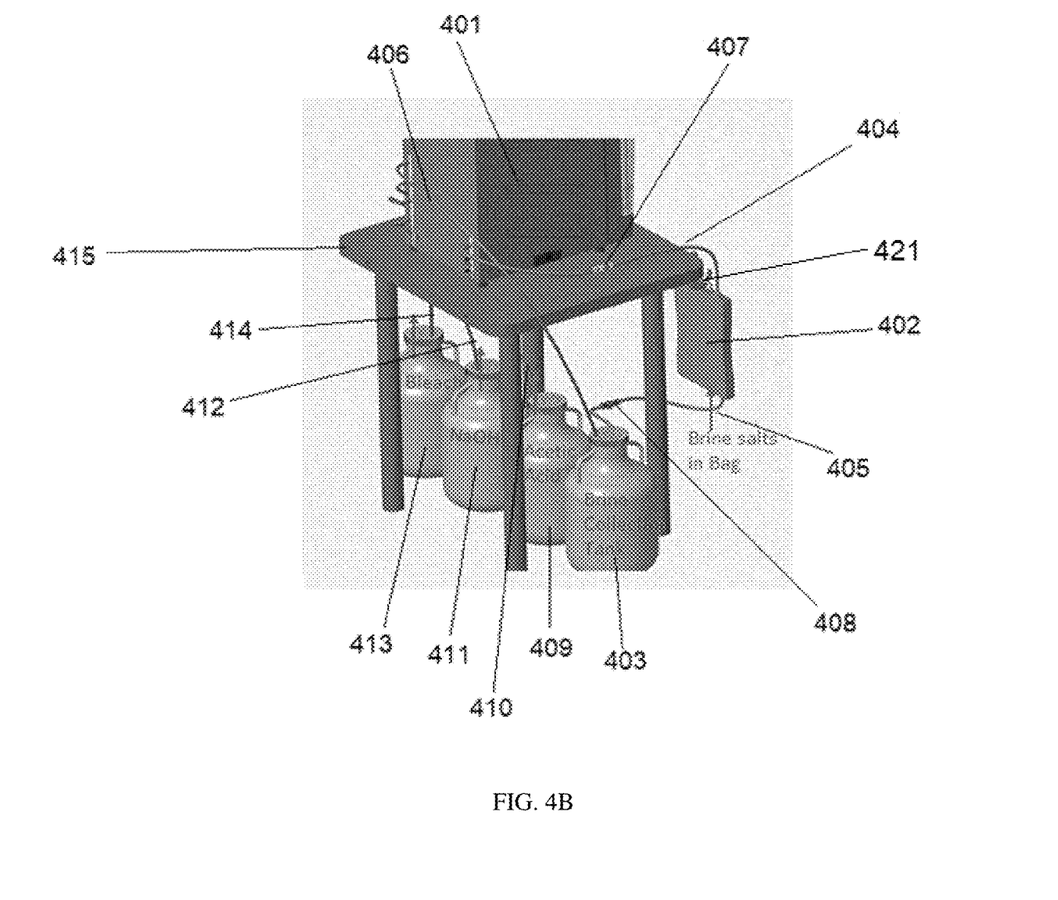

FIGS. 4A-B show a sorbent recharger 401 using a salt bag 402 as described. FIG. 4A is a front view of the sorbent recharger 401, while FIG. 4B is a perspective view of the sorbent recharger 401. As illustrated in FIG. 4A, a salt bag 402 can be fluidly connected to the sorbent recharger 401. Water from a water source (not shown) can be pumped through an inlet of the salt bag 402 into a porous water permeable inner bag (not shown) of salt bag 402 containing sodium chloride and sodium acetate through fluid line 404. The brine solution formed can exit the inner bag of the salt bag 402 and flow through fluid line 405 into brine container 403. Fluid can be recirculated in a flow path from the outlet of the salt bag 402, through fluid line 405 and into the brine container 403, out of brine container 403 through fluid line 406 back to sorbent recharger 401, and then back into the salt bag 402 through fluid line 404. The brine solution can be recirculated in the flow path until a homogeneous solution is formed, or for a preset period of time. While the brine solution is recirculating, acetic acid from acetic acid source 409 can be pumped through fluid line 410 into sorbent recharger 401, where the acetic acid is added to the recirculating brine solution. After a homogeneous brine solution is formed, the brine solution can be collected in brine container 403. The salt bag 402 can connect to fluid lines 404 and 405 through any means known in the art. As described, the salt bag 402 can be mounted on the system using hook 421, or by any other method.

The sorbent recharger 401 can include one or more receiving compartments for receiving reusable sorbent modules. As illustrated in FIG. 4A, the sorbent recharger 401 includes a first receiving compartment 417 for receiving a zirconium phosphate sorbent module 416. To recharge the zirconium phosphate in the zirconium phosphate sorbent module 416, the generated brine solution in brine container 403 is pumped through the zirconium phosphate sorbent module 416, replacing potassium, calcium, magnesium, and ammonium ions bound to the zirconium phosphate with sodium and hydrogen ions.

In certain embodiments, additional receiving compartments can be included. For example, the sorbent recharger 401 shown in FIG. 4A includes a second receiving compartment 418 for receiving a zirconium oxide sorbent module 419. Additional chemicals can be included for recharging the zirconium oxide in zirconium oxide sorbent module 419. To recharge zirconium oxide, a basic solution can be pumped through the zirconium oxide sorbent module 419. Sodium hydroxide from sodium hydroxide source 411 can be pumped through fluid line 412 into sorbent recharger 401 and through the zirconium oxide sorbent module 419. Bleach from bleach source 413 can be pumped through fluid line 414 into sorbent recharger 401 and through the zirconium oxide sorbent module 419 to disinfect the zirconium oxide sorbent module 419. Alternatively, a sorbent recharger can include two receiving compartments to recharge two different zirconium phosphate sorbent modules. In any embodiment, the sorbent recharger 401 can include any number of receiving compartments for recharging any number of zirconium phosphate and/or zirconium oxide sorbent modules.

The sorbent recharger can include a graphical user interface 420 that can be used to control recharging of the sorbent materials. Through graphical user interface 420, the user can initiate, stop, and otherwise control the preparation of the brine solution and the recharging process. Further, any errors, alerts, or other messages can be provided to the user through graphical user interface 420. In FIGS. 4A-B, the sorbent recharger 401 is small enough to fit on table 415. However, larger sorbent rechargers can be used for recharging additional materials.

FIG. 4B shows the rear of sorbent recharger 401. As described, sorbent recharger 401 can be connected to brine container 403 through fluid line 406, acetic acid source 409 through fluid line 410, sodium hydroxide source 411 through fluid line 412 and bleach source 413 through fluid line 414. In FIG. 4B the connection between the salt bag 402 and sorbent recharger 401 is shown as quick connector 407. Similarly, the connection between brine container 403 and salt bag 402 is shown as quick connector 408. Quick connectors allow fluid lines to be connected by snapping connectors on each line together. However, other connectors that can form fluid passages can be used as known by those of skill in the art.

Figure 5:
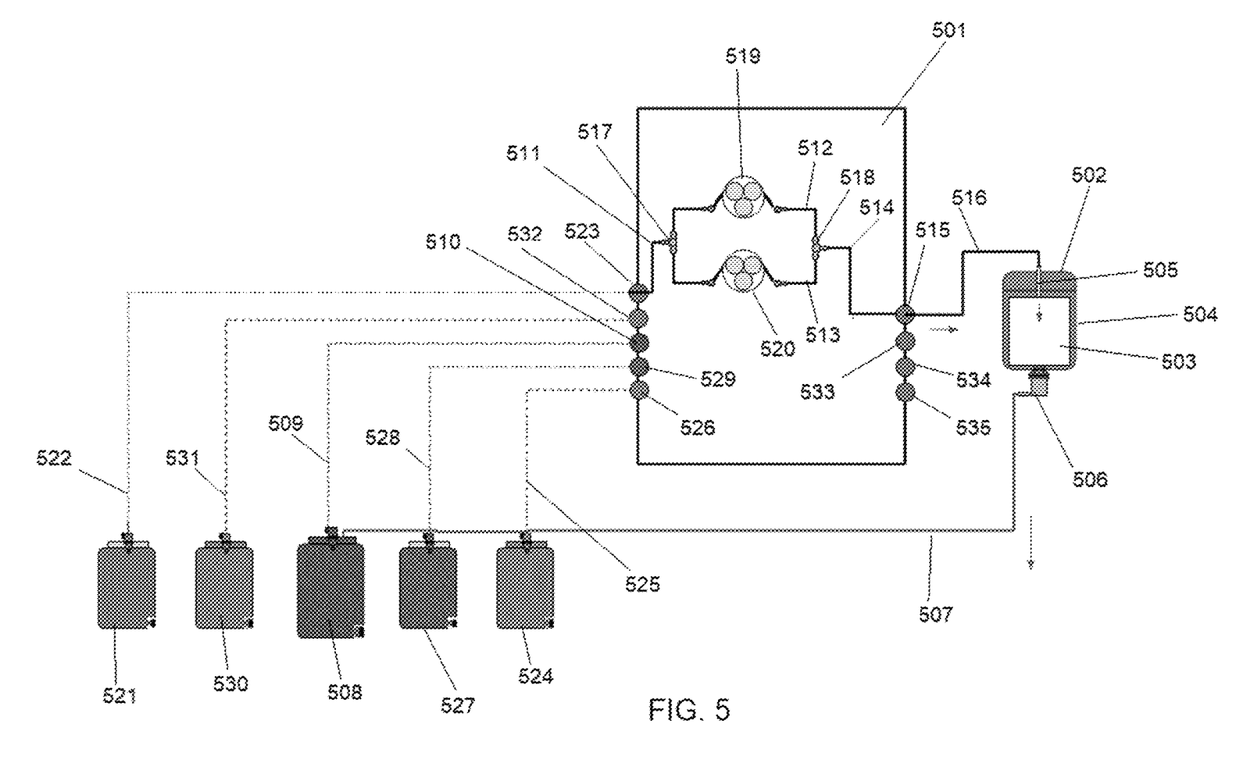
FIG. 5 shows a flow path for a sorbent recharger using a salt bag.

FIG. 5 shows a flow diagram for a recharger system using a salt bag. The salt bag 502 can include a non-porous water impermeable outer bag 504 and a porous water permeable inner bag 503. Solid sodium chloride and solid sodium acetate can be placed in the inner bag 503. Water from water source 521 can be pumped through water line 522 and port 523 into sorbent recharger 501. As illustrated in FIG. 5, in certain embodiments the sorbent recharger 501 can use two pumps 519 and 520. Using two pumps allows fluid from multiple sources to be mixed in-line rather than using mixing chambers. However, one of skill in the art will understand that a single pump system can also be used. From inlet port 523, the water is pumped through fluid line 511 and T-junction 517 into fluid lines 512 and 513. The water is pumped through T-junction 518 and fluid line 514 to port 515. From port 515, the water can flow through fluid line 516 and into the inner bag 503 of salt bag 502 through inlet 505.

The water can dissolve at least a portion of the sodium acetate and sodium chloride in inner bag 503 and pass out of the inner bag 503 into outer bag 504. The solution thus formed exits the salt bag 502 through outlet 506 into fluid line 507 and brine container 508. The brine solution can be recirculated through the flow path from brine container 508, through fluid line 509 and port 510 of the sorbent recharger 501 into fluid line 511, where the brine solution follows the same pathway as the water back into salt bag 502. During recirculation of the brine solution, acetic acid from acetic acid source 524 can be pumped through fluid line 525 and port 526 for addition to the brine solution recirculating in the flow path. Once the sodium acetate and sodium chloride are fully dissolved, the acetic acid is added, and a homogeneous brine solution is formed, the brine solution can be collected in brine container 508.

To recharge zirconium phosphate, a zirconium phosphate sorbent module can be placed in a receiving compartment (not shown) of the sorbent recharger 501. An inlet of the zirconium phosphate sorbent module can be connected to fluid line 514, and an outlet of the zirconium phosphate sorbent module can be fluidly connected to a drain or collection container (not shown). The control system can operate pump 519 and/or pump 520 to pump brine solution from brine container 508 through the zirconium phosphate sorbent module.

As described, in certain embodiments, the sorbent recharger 501 can include a receiving compartment for receiving a zirconium oxide sorbent module (not shown). To recharge zirconium oxide in a zirconium oxide sorbent module, bleach can be pumped from bleach container 530, through fluid line 531 to port 532. A separate flow path can direct the bleach solution through the zirconium oxide sorbent module to a drain or collection container. Sodium hydroxide from sodium hydroxide container 527 can be pumped through fluid line 528 and port 529, and then through the zirconium oxide sorbent module. Additional outlet ports can be included on the sorbent recharger 501, including outlet port 533, outlet port 534, and outlet port 535 for connection to waste collection containers, drains, or other components.

One of skill in the art will understand that FIG. 5 is a simplified diagram of a non-limiting embodiment of a sorbent recharger 501. Additional components, such as valves, sensors, additional pumps, and additional fluid lines can be included as necessary. The control system can be programmed to control the pumps and valves to direct fluid through the proper flow paths for generating the brine solution and recharging the sorbent materials.

The described systems and methods allow for a "just in time" brine preparation. Rather than storing large quantities of premade brine solution, the salt bag system allows for preparation of the brine solution immediately before use. The time required to generate the brine solution using a salt bag can vary, but generally the generation of the brine solution will be under 1 hour, or about 45 minutes.

One skilled in the art will understand that various combinations and/or modifications and variations can be made in the described systems and methods depending upon the specific needs for operation. Various aspects disclosed herein may be combined in different combinations than the combinations specifically presented in the description and accompanying drawings. Moreover, features illustrated or described as being part of an aspect of the disclosure may be used in the aspect of the disclosure, either alone or in combination, or follow a preferred arrangement of one or more of the described elements. Depending on the example, certain acts or events of any of the processes or methods described herein may be performed in a different sequence, may be added, merged, or left out altogether (e.g., certain described acts or events may not be necessary to carry out the techniques). In addition, while certain aspects of this disclosure are described as performed by a single module or unit for purposes of clarity, the techniques of this disclosure may be performed by a combination of units or modules associated with, for example, a medical device.

What is claimed is:

1. A system, comprising:
   a sorbent recharger; the sorbent recharger comprising:
   i) a receiving compartment for a zirconium phosphate sorbent module;
   ii) at least a first fluid line fluidly connectable to an inlet of the zirconium phosphate sorbent module in the receiving compartment;
   iii) at least a second fluid line fluidly connectable to an outlet of the zirconium phosphate sorbent module;
   iv) at least one pump;
   a brine container fluidly connectable to the first fluid line;
   a salt bag; the salt bag comprising an inlet fluidly connectable to a water source and an acetic acid source; and an outlet fluidly connectable to the brine container; the salt bag containing sodium chloride and sodium acetate; and
   a control system; the control system programmed to:
   i) pump a preset volume of fluid from the water source through the salt bag;
   ii) recirculate fluid in a first flow path from the outlet of the salt bag to the brine container and then to the inlet of the salt bag; and to
   iii) pump a preset volume of acetic acid into the first flow path.

2. The system of claim 1, wherein the salt bag is a double layer bag comprising an outer bag that is water impermeable and an inner bag that is at least partly water permeable.

3. The system of claim 2, wherein the sodium chloride and sodium acetate are initially in the inner bag of the salt bag.

4. The system of claim 2, wherein the inner bag has a water impermeable portion at a top of the inner bag.

5. The system of claim 2, wherein the inlet of the salt bag is connected to an interior of the inner bag; and wherein the outlet of the salt bag is connected to an exterior of the inner bag.

6. The system of claim 1, the control system further programmed to pump fluid from the brine container through the zirconium phosphate sorbent module.

7. The system of claim 1, the control system programmed to recirculate fluid in the first flow path until a homogeneous solution is formed in the first flow path.

8. The system of claim 1, the salt bag further comprising a spring-loaded valve at the inlet.

9. The system of claim 1, the salt bag further comprising a spring-loaded valve at the outlet.

10. A method for generating a brine solution for recharging zirconium phosphate using the system of claim 1; comprising the steps of:
    pumping water from the water source to the salt bag through the inlet of the salt bag; the salt bag containing sodium chloride and sodium acetate;
    recirculating fluid from the outlet of the salt bag, to the brine container, and back to the inlet of the salt bag in a first flow path;
    pumping acetic acid into the first flow path; and
    collecting fluid from the first flow path into the brine container to generate the brine solution.

11. The method of claim 10, wherein the salt bag is a double layer bag comprising an outer bag that is water impermeable and an inner bag that is at least partly water permeable.

12. The method of claim 11, wherein the sodium chloride and sodium acetate are initially in the inner bag of the salt bag.

13. The method of claim 11, wherein the inner bag has a water impermeable portion at a top of the inner bag.

14. The method of claim 10, wherein the brine container is fluidly connected to the sorbent recharger; and further comprising the step of pumping the brine solution through a zirconium phosphate sorbent module in the sorbent recharger.

15. The method of claim 10, wherein the fluid is recirculated in the first flow path until a homogenous solution is generated.

16. A salt bag for use in recharging zirconium phosphate, the salt bag comprising:
    a water impermeable outer bag;
    a water permeable inner bag;
    an inlet fluidly connectable to a water source; and
    an outlet fluidly connectable to a brine container;
    the salt bag containing sodium chloride and sodium acetate.

17. The salt bag of claim 16, further comprising a spring-loaded valve at the inlet.

18. The salt bag of claim 16, further comprising a spring-loaded valve at the outlet.

19. The salt bag of claim 16, wherein the inner bag has a water impermeable portion at a top of the inner bag.

20. The salt bag of claim 16, wherein the inlet is connected to an interior of the inner bag; and wherein the outlet is connected to an exterior of the inner bag.

* * * * *